United States Patent [19]

Gray et al.

[11] Patent Number: 5,595,888

[45] Date of Patent: *Jan. 21, 1997

[54] RECOMBINANT METHODS OF MAKING GAMMA INTERFERON COMPOSITIONS

[75] Inventors: Patrick W. Gray, San Francisco; Ernst H. Rinderknecht, San Carlos, both of Calif.

[73] Assignee: Genentech, Inc., South San Francisco, Calif.

[*] Notice: The portion of the term of this patent subsequent to Feb. 23, 2005, has been disclaimed.

[21] Appl. No.: 221,542

[22] Filed: Mar. 24, 1994

Related U.S. Application Data

[60] Continuation of Ser. No. 837,642, Feb. 14, 1992, abandoned, which is a division of Ser. No. 93,455, Sep. 4, 1987, abandoned, which is a division of Ser. No. 584,217, Feb. 27, 1984, Pat. No. 4,855,238, which is a continuation-in-part of Ser. No. 562,009, Dec. 16, 1983, abandoned.

[51] Int. Cl.[6] .............................. C12N 15/23; C12N 1/21
[52] U.S. Cl. ................. 435/69.51; 530/351; 424/85.5
[58] Field of Search .................. 435/69.51, 252.3, 435/252.33; 530/351, 412; 424/85.5

[56] References Cited

U.S. PATENT DOCUMENTS

| | | | |
|---|---|---|---|
| 4,285,929 | 8/1981 | Sugimoto et al. | 424/85.6 |
| 4,332,892 | 6/1982 | Ptashne et al. | 435/69.7 |
| 4,338,397 | 7/1982 | Gilbert et al. | 435/69.1 |
| 4,382,027 | 5/1983 | Braude | 530/351 |
| 4,457,867 | 7/1984 | Ishida et al. | 530/324 |
| 4,599,306 | 7/1986 | Altrock | 435/7.93 |
| 4,604,284 | 8/1986 | Kung et al. | 424/85.5 |
| 4,727,138 | 2/1988 | Goeddel et al. | 536/23.52 |
| 4,762,791 | 8/1988 | Goeddel et al. | 435/240.2 |
| 4,855,238 | 8/1989 | Gray et al. | 435/243 |
| 4,855,409 | 8/1989 | Masakazu et al. | 530/351 |
| 4,925,793 | 5/1990 | Goeddel et al. | 435/69.51 |
| 4,929,554 | 5/1990 | Goeddel et al. | 435/172.3 |
| 5,004,689 | 4/1991 | Fiers et al. | 435/69.51 |

FOREIGN PATENT DOCUMENTS

| | | |
|---|---|---|
| 0028033 | 5/1981 | European Pat. Off. . |
| 0063482 | 10/1982 | European Pat. Off. . |
| 0077670 | 4/1983 | European Pat. Off. . |
| 0087686 | 9/1983 | European Pat. Off. . |
| 0089676 | 9/1983 | European Pat. Off. . |
| 0088540 | 9/1983 | European Pat. Off. . |
| 0095350 | 11/1983 | European Pat. Off. . |
| 0103898 | 3/1984 | European Pat. Off. . |
| 0112976 | 7/1984 | European Pat. Off. . |
| 0121157 | 10/1984 | European Pat. Off. . |
| 0126230 | 11/1984 | European Pat. Off. . |
| 0136694 | 4/1985 | European Pat. Off. . |
| 0137691 | 4/1985 | European Pat. Off. . |
| 0144064 | 6/1985 | European Pat. Off. . |
| 0145174 | 6/1985 | European Pat. Off. . |
| 2040292 | 8/1980 | United Kingdom . |
| 2063882 | 6/1981 | United Kingdom . |
| 2068970 | 8/1981 | United Kingdom . |
| 2071108 | 9/1981 | United Kingdom . |
| 2091268 | 7/1982 | United Kingdom . |
| 813498 | 12/1981 | WIPO . |
| 8304053 | 11/1983 | WIPO . |
| 8502624 | 6/1985 | WIPO . |

OTHER PUBLICATIONS

Novokhatskii et al, *Chemical Abstract* 96, No. 120770e (1982) first pub. in Dokl. Akad. Nauk. SSSR 261, 997 (1981).
Goeddel et al, *Nature* 287, 411 (1980).
Hamer et al, *Nature* 281, 35 (1979).
Weissman, in *Interferon* 3, (Gresser, Ed: Academic Press) 101 (1981).
Vilcek, in *Interferon* 4, (Academic Press) 129 (1982).
Murray, *Annals of Internal Medicine* 98, 1016 (1983).
Maniatis et al, *Molecular Cloning, A Laboratory Manual*, 1982, Cold Spring Harbor Laboratory, Cold Spring Harbor, N.Y., pp. 418–419.
Devos et al, "Molecular Cloning of Human Immune Interferon cDNA and its expression in Eukaryotic cells", *Nucleic Acids*, Res. 10:2487 (1982).
Fiers et al, "Molecular–biological studies on human fibroblast interferon, immune interferon and Interleukin 2 Genes", in *The Biology of the Interferon System* 1983, DeMaeyer et al (ed.), 1983, Elsevier Science Publishers, Amsterdam, pp. 3–8.
Alton et al, "Production, Characterization and biological effects of Recombinant DNA Derived Human IFN–alpha and IFN–gamma analogs", in *The Biology of the Interferon System* 1983, DeMaeyer et al (ed.), 1983, Elsevier Science Publishers, Amsterdam, pp. 119–128.
Hsieh et al, *J. Biol. Chem.*, vol. 258, pp. 2548–2554, (1983).
Yamashita et al., *Archives of Biochemistry*, vol. 225, pp. 993–996 (1983).
Nakamura et al., *Virology*, vol. 95, pp. 8–23, (1979).
*Concanavalin A*, Pharmacia Fine Chemicals.
*Gene Expression*, vol. 2, Eucaryotic Chromosomes, Lewin 1974, John Wiley & Sons, New York, p. 148.
Grey, et al, "Expression of Human Immune Interferon cDNA in *E. Coli* and Monkey Cells", Nature 295; 503 (1982).
Yip et al, *Science* 215, 411 (1982).
*Genetic Engineering Letter* 2, No. 17 "Artificial Gene for Gamma Interferon Reported by Japanese Scientist" (1982).

(List continued on next page.)

*Primary Examiner*—David L. Fitzgerald
*Attorney, Agent, or Firm*—Walter H. Dreger

[57] ABSTRACT

Provided are methods for the production of mixtures of interferon (IFN)-γ polypeptides. The methods employ a single species of IFN-γ DNA having codons for Met-Gln and for residues 2–143 of the mature human IFN-γ amino acid sequence. Expression of such DNA in a suitable recombinant host cell affords a mixture of polypeptides having N-terminal Met-Gln, H-Gln, or H-pyroglutamate residues and C-termini at Arg[139], Ser[142], or Gln[143] of the mature IFN-γ sequence. The polypeptides so produced exhibit the antiviral and antiproliferative activities as well as the acid lability characteristic of native human IFN-γ.

5 Claims, 4 Drawing Sheets

OTHER PUBLICATIONS

Newmark, *Nature* 294, 7 (1981).
Luskey et al, *Nature* 293, 79 (1981).
*Research Disclosure*, "Purification of Interferon mRNA by Hybridising Induced Material to cDNA", (10 July 1979).
O'Malley, *Methods in Enzymology*, vol. 78, pp. 540–545, (1981).
*Life*, p. 50, (May 1980).
*Time*, p. 60, (Mar. 31, 1980).
Devos, et al, *Nucl. Acids. Res.* 10, 2487 (1982).
Epstein, *Nature* 295, 453 (1982).
Epstein, in *Interferon* 3, (Gresser, ed: Academic Press) 13 (1981).
Nathan et al, *Nature* 292, 842 (1981).
Dianzani et al, *Nature* 283, 400 (1980).
Wallace et al, *Fed. Proc.* 40, 1574 (1981).
Wallace et al, *Biochem. Biophys. Res. Comm.* 100, 865 (1981).
Taniguchi et al, *Proc. Natl. Acad. Sci.* USA 78, 3469 (1981).
Epstein, L. B., *Fed. Proc.* 40, 56 (1981).
Vilcek, J. et al, *Microbiol.*, 204 (1980).
Capon et al, *The Third Annual International Congress for Interferon Research, Miami, Florida, 1982, p. 15*.
Derynck et al, *Experimental Manipulation of Gene Expression*, p. 247 (1983).
de Ley, M. et al; *Euro. J. Immunol.* 10, 877 (1980).
Yip, Y. K. et al; *Proc. Nat. Acad. Sci.* (USA), 78, 1601 (1978).
Berger, S. L. et al, *J. Biol. Chem.* 255, 2955 (1980).
Botstein et al, *Recomb. DNA Tech. Bull.* 2, 49 (1979).

```
TGAAGATCAGCTATTAGAAGAGAAAGATCAGTTAAGTCCTTTGGACCTGATCAGCTTGATACAAG
                                                 50 s1
                                             met lys tyr thr ser
AACTACTGATTTCAACTTCTTTGGCTTAATTCTCTCGGAAACG  ATG AAA TAT ACA AGT
                        100 s10
tyr ile leu ala phe gln leu cys ile val leu gly ser leu
TAT ATC TTG GCT TTT CAG CTC TGC ATC GTT TTG GGT TCT CTT
                                    150 s23 1                                             10
gly cys tyr cys GLN ASP PRO TYR VAL LYS GLU ALA GLU ASN LEU LYS
GGC TGT TAC TGC CAG GAC CCA TAT GTA AAA GAA GCA GAA AAC CTT AAG 20
LYS TYR PHE ASN ALA GLY HIS SER ASP VAL ALA ASP ASN GLY
AAA TAT TTT AAT GCA GGT CAT TCA GAT GTA GCG GAT AAT GGA
                                                250

30                                          40
THR LEU PHE LEU GLY ILE LEU LYS ASN TRP LYS GLU GLU SER ASP ARG
ACT CTT TTC TTA GGC ATT TTG AAG AAT TGG AAA GAG GAG AGT GAC AGA
                                                        300

50
LYS ILE MET GLN SER GLN ILE VAL SER PHE TYR PHE LYS LEU
AAA ATA ATG CAG AGC CAA ATT GTC TCC TTT TAC TTC AAA CTT 60                              70
PHE LYS ASN PHE LYS ASP ASP GLN SER ILE GLN LYS SER VAL GLU THR
TTT AAA AAC TTT AAA GAT GAC CAG AGC ATC CAA AAG AGT GTG GAG ACC
    350

80
ILE LYS GLU ASP MET ASN VAL LYS PHE PHE ASN SER ASN LYS
ATC AAG GAA GAC ATG AAT GTC AAG TTT TTC AAT AGC AAC AAA
        400

90                              100
LYS LYS ARG ASP ASP PHE GLU LYS LEU THR ASN TYR SER VAL THR ASP
AAG AAA CGA GAT GAC TTC GAA AAG CTG ACT AAT TAT TCG GTA ACT GAC
                450

110
LEU ASN VAL GLN ARG LYS ALA ILE HIS GLU LEU ILE GLN VAL
TTG AAT GTC CAA CGC AAA GCA ATA CAT GAA CTC ATC CAA GTG
                500
```

FIG._1A

```
                        120                                              130
MET ALA GLU LEU SER PRO ALA ALA LYS THR GLY LYS ARG LYS ARG SER
ATG GCT GAA CTG TCG CCA GCA GCT AAA ACA GGG AAG CGA AAA AGG AGT
                                    550

140         143 STOP
GLN MET LEU PHE ARG GLY ARG ARG ALA SER GLN
CAG ATG CTG TTT CGA GGT CGA AGA GCA TCC CAG TAA TGGTTGT
                                        600

CCTGCCTGCAATATTTGAATTTTAAATCTAAATCTATTTATTAATATTTAACATTATTTATATG
                        650

GGGAATATATTTTTAGACTCTCATCAATCAAATAAGTATTTATAATAGCAACTTT
            700

TGTGTAATGAAAATGAATATCTATTAATATATGTATTATTTATAATTCCTATATCCTGTGACTG
                    750

TCTCACTTAATCCTTTGTTTTCTGACTAATTAGGCAAGGCTATGTGATTACAAGG
 800                                                  850

CTTTATCTCAGGGGCCAACTAGGCAGCCAACCTAAGCAAGATCCCATGGTTGTGTGTTTATTTC
                                        900

ACTTGATGATACAATGAACACTTATAAGTGAAGTGATACTATCCAGTTACTGCCG
                        950

GTTTGAAAATATGCCTGCAATCTGAGCCAGTGCTTTAATGGCATGTCAGACAGAACTTGAATGT
                    1000

GTCAGGTGACCCTGATGAAAACATAGCATCTCAGGAGATTTCATGCCTGGTGCTT
            1050

CCAAATATTGTTGACAACTGTGACTGTACCCAAATGGAAAGTAACTCATTTGTTAAAATTATCA
   1100                                                       1150

ATATCTAATATATATGAATAAAGTGTAAGTTCACAACTAAAAAAAAAAAAAAAAAAAA
                        1200
```

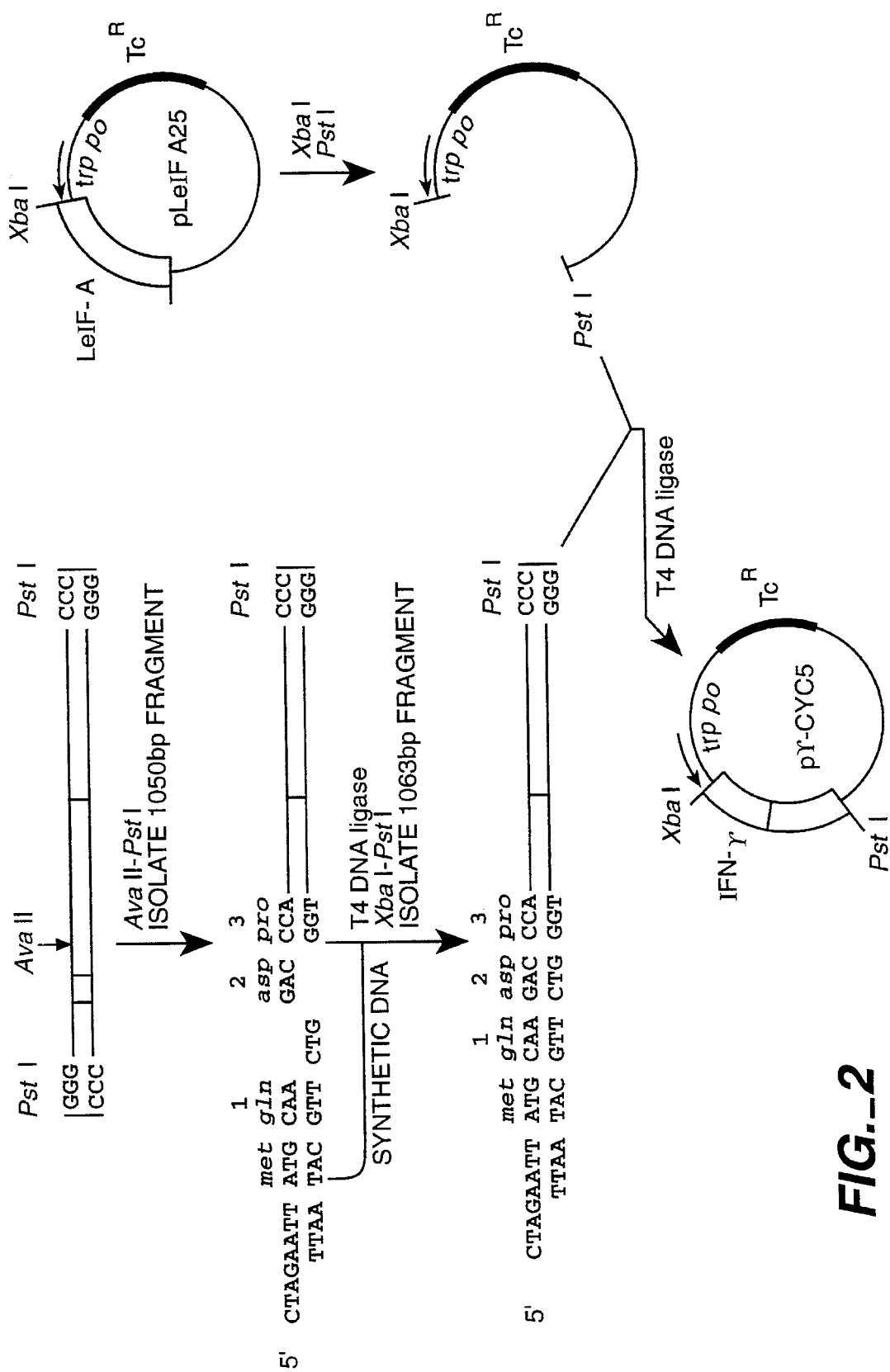
FIG._2

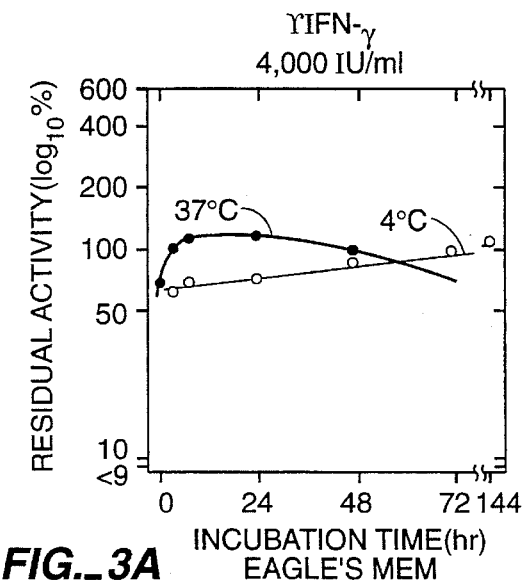
FIG._3A INCUBATION TIME(hr) EAGLE'S MEM
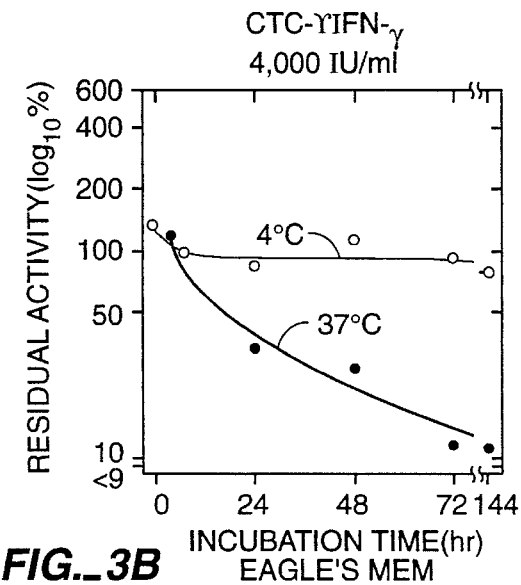
FIG._3B INCUBATION TIME(hr) EAGLE'S MEM
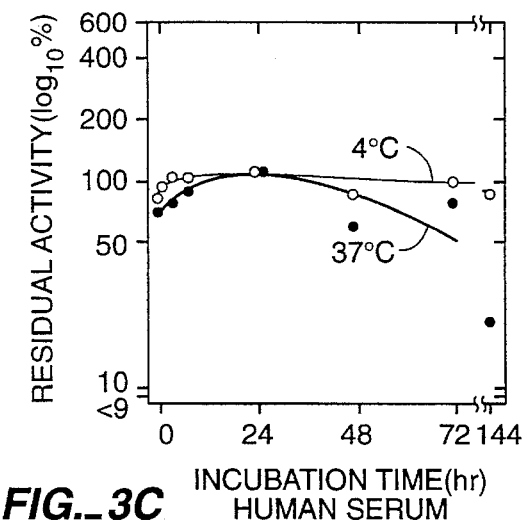
FIG._3C INCUBATION TIME(hr) HUMAN SERUM
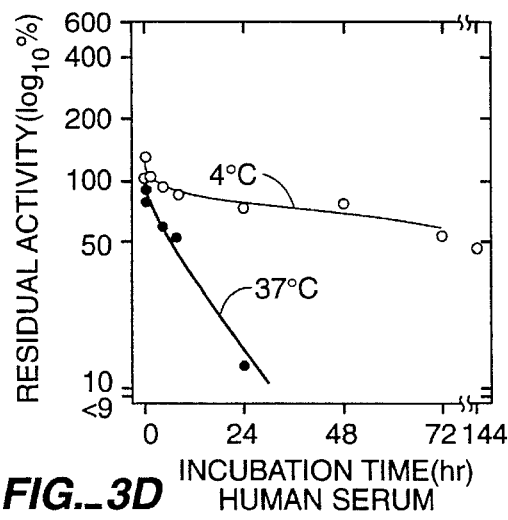
FIG._3D INCUBATION TIME(hr) HUMAN SERUM
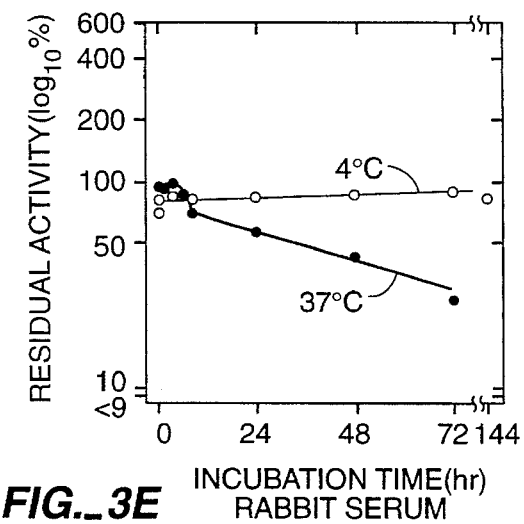
FIG._3E INCUBATION TIME(hr) RABBIT SERUM
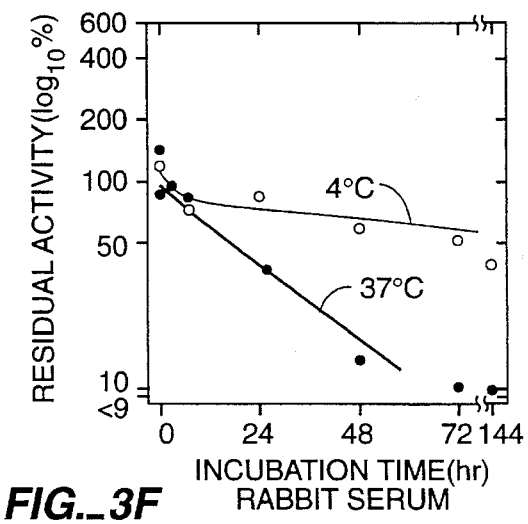
FIG._3F INCUBATION TIME(hr) RABBIT SERUM

RECOMBINANT METHODS OF MAKING GAMMA INTERFERON COMPOSITIONS

This is a continuation of application Ser. No. 07/837,642 filed 14 Feb. 1992, now abandoned, which is a divisional of application Ser. No. 07/093,455 filed 4 Sep. 1987, now abandoned, which is a divisional of application Ser. No. 06/584,217 filed 27 Feb. 1984, now U.S. Pat. No. 4,855,238, which is a continuation-in-part of application Ser. No. 06/562,009 filed 16 Dec. 1983, now abandoned.

FIELD OF THE INVENTION

The present invention relates to the field of recombinant DNA technology, to means and methods utilizing such technology in the preparation of recombinant gamma interferons having enhanced stability, to their production and to the various products of such production and their uses.

CROSS-REFERENCE TO RELATED APPLICATION

This application is related in subject to application Ser. No. 06/312,489 filed Oct. 19, 1981 by Goeddel and Gray for "Human Immune Interferon", now abandoned, the disclosure of which is incorporated herein by reference.

BACKGROUND OF THE INVENTION

The publications and other materials used herein to illuminate the background of the invention and in particular cases to provide additional details respecting its practice are incorporated herein by reference and for convenience are numerically referenced in the following text and respectively grouped in the appended bibliography.

Human interferons can be classified in three groups on the basis of different antigenicity and biological and biochemical properties. The first group comprises a family of leukocyte interferons which are normally produced mainly by constituent cells of human blood upon viral induction. These have been microbially produced and found to be biologically active (1,2,3). Their biological properties have prompted their use in the clinic as therapeutic agents for the treatment of viral infections and malignant conditions (4).

In the second group is human fibroblast interferon, normally produced by fibroblasts upon viral induction, which has likewise been microbially produced and found to exhibit a wide range of biological activities (5). Clinical trials also indicate its potential therapeutical value. The leukocyte and fibroblast interferons exhibit very clear similarities in their biological properties despite the fact that the degree of homology at the amino acid level is relatively low. Both groups of interferons contain from about 165 to about 166 amino acids and are acid stable proteins.

Human gamma interferon (also variously referred to as immune interferon, $\gamma$-interferon, IIF or IFN-$\gamma$) exhibits the antiviral and anti-proliferative properties characteristic of the interferons but, in contrast to leukocyte and fibroblast interferons, is pH 2 labile. Prior to the production of gamma interferons via recombinant DNA technology, it had been produced mainly upon mitogenic induction of lymphocytes. Human gamma interferon is clearly antigenically distinct from the leukocyte and fibroblast interferons. Gray, Goeddel and co-workers were the first to report expression of a recombinant gamma interferon (6), which has proven to exhibit the characteristic properties of human gamma interferon, i.e., anti-viral and anti-proliferative activity coupled with pH 2 lability. The recombinant gamma interferon of Gray and Goeddel, as produced in *E. coli*, consisted of 146 amino acids, the N-terminal portion of the molecule commencing with the sequence CYS-TYR-CYS-. Derynck and others subsequently reported (7) a further recombinant gamma interferon having the same N-terminus and a single amino acid substitution, the polypeptide perhaps constituting an allelic variant of that earlier reported in reference (6). Other workers have reported the production of still further recombinant gamma interferons in which one or more of the amino acids present in Goeddel and Gray's original publication (6) have allegedly been substituted.

For example, Alton et al. (17) report on a series of IFN-gammas wherein a single amino acid substitution at position 81 of the Gray et al. (6) gamma interferon resulted in an IFN-gamma that retained only 70 percent of the activity (on a relative basis) and wherein an additional deletion of the cys-tyr-cys at positions 1, 2, 3 of this IFN-gamma further reduced relative activity resulting in an IFN-gamma having only 49 percent of the Gray et al. (6) gamma interferon.

In our hands, recombinant gamma interferons whose N-terminal amino acid sequence comprises cysteine residues have proven problematic from the standpoint of oligomerization which may involve participation of sulfhydryl groups of one or more of the cysteine residues in disulfide bond formation. Our inability to completely reduce these putative disulfide linkages suggests the problem may be more complex, possibly also involving reaction through the hydroxyl function of the cysteine-bounded tyrosine residue. These recombinant interferons have proven somewhat unstable and, whether resulting from such instability or otherwise, have proven of less than optimal utility.

SUMMARY OF THE INVENTION

The present invention relates to recombinant gamma interferons having enhanced stability and activity. In the most preferred embodiment we provide a recombinant gamma interferon comprising the amino acid sequence (hereinafter "full sequence"), extending from the N-terminus:

```
X—Y—ASP—PRO—TYR—VAL—LYS—GLU—ALA—GLU—ASN—LEU—LYS—LYS—TYR—PHE—ASN—ALA—
1   2   3    4    5    6    7    8    9    10   11   12   13   14   15   16   17

GLY—HIS—SER—ASP—VAL—ALA—ASP—ASN—GLY—THR—LEU—PHE—LEU—GLY—ILE—LEU—LYS—
18   19   20   21   22   23   24   25   26   27   28   29   30   31   32   33   34

ASN—TRP—LYS—GLU—GLU—SER—ASP—ARG—LYS—ILE—MET—GLN—SER—GLN—ILE—VAL—SER—
35   36   37   38   39   40   41   42   43   44   45   46   47   48   49   50   51

PHE—TYR—PHE—LYS—LEU—PHE—LYS—APN—PHE—LYS—ASP—ASP—GLN—SER—ILE—GLN—LYS—
52   53   54   55   56   57   58   59   60   61   62   63   64   65   66   67   68
```

```
SER—VAL—GLU—THR—ILE—LYS—GLU—ASP—MET—ASN—VAL—LYS—PHE—PHE—ASN—SER—ASN—
 69   70   71   72   73   74   75   76   77   78   79   80   81   82   83   84   85

LYS—LYS—LYS—ARG—ASP—ASP—PHE—GLU—LYS—LEU—THR—ASN—TYR—SER—VAL—THR—ASP—
 86   87   88   89   90   91   92   93   94   95   96   97   98   99  100  101  102

LEU—ASN—VAL—GLN—ARG—LYS—ALA—ILE—HIS—GLU—LEU—ILE—GLN—VAL—MET—ALA—GLU—
103  104  105  106  107  108  109  110  111  112  113  114  115  116  117  118  119

LEU—SER—PRO—ALA—ALA—LYS—THR—GLY—LYS—ARG—LYS—ARG—SER—GLN—MET—LEU—PHE—
120  121  122  123  124  125  126  127  128  129  130  131  132  133  134  135  136

ARG—GLY—ARG—ARG—ALA—SER—GLN
137  138  139  140  141  142  143
``` wherein X is a methionine residue or hydrogen and Y is a glutamine residue or, where X is a hydrogen, either a glutamine or pyroglutamate residue, as well as various analogs thereof in which specified portions of the carboxy terminal of the foregoing sequence are absent. The invention also provides corresponding cloned genes, expression vectors comprising them, and transformants useful in the production through recombinant DNA technology of the interferons of the invention. The preferred recombinant gamma interferons of the invention (as compared to those previously characterized in the literature) appear to most closely approximate the true amino acid sequence of native gamma interferon, the latter of which we have now purified from native sources and fully characterized. Preferred embodiments of the invention exhibit greatly improved stability and activity relative to those previously described in the literature.

IN THE DRAWINGS

The manner in which these and other objects of the invention are attained will be apparent from the detailed description which follows and from the accompanying drawings, in which:

FIG. 1 (FIG. 1A and FIG. 1B) illustrates amino acids 1 through 143 of a recombinant gamma interferon of the present invention and DNA sequence encoding the amino acid sequence preceded by a signal sequence, which DNA sequence is flanked by regions of 5'- and 3'-untranslated DNAs.

FIG. 2 illustrates schematically a plasmid coding for direct synthesis of a recombinant gamma interferon of the present invention in E. coli and its preparation.

FIG. 3 (FIG. 3A, FIG. 3B, FIG. 3C, FIG. 3D, FIG. 3E, FIG. 3F) records data demonstrating the enhanced stability of gamma interferon prepared according to the present invention.

DETAILED DESCRIPTION

We have learned that native human gamma interferon (i.e., that arising from mitogen induction of human peripheral blood lymphocytes and subsequent purification) is a polypeptide which lacks the CYS-TYR-CYS- N-terminus assigned by Gray et al. to the recombinant gamma interferon whose sequence is depicted in (6). Tryptic digests of highly purified native gamma interferon in our hands included sequences whose amino acid composition generally corresponded to that of the N-terminal portion of the Gray et al. recombinant gamma interferon of (6), less CYS-TYR-CYS. Amino acid sequence analysis from the N-terminus of native gamma interferon proved unavailing, giving rise to the inference that the alpha amino acid at the N-terminus of the molecule was protected. Since the first amino acid beyond the second cysteine of Gray et al. (6) for which the cDNA coded was GLN (glutamine), we surmised that cyclization of the GLN residue had left instead pyroglutamate, such that the N-terminus was blocked. Removal of pyroglutamate with pyroglutamate aminopeptidase left a free alpha amino group associated with ASP, the next encoded amino acid, and sequence analysis could proceed, permitting the first reported characterization of native human gamma interferon.

Appropriate alteration of cDNA for CYS-TYR-CYS-containing recombinant human gamma interferon permitted the direct expression in E. coli of novel recombinant gamma interferon from a cDNA encoding the protein whose full sequence is set out supra, X being MET and Y being GLN. The N-terminal methionine is an artifact encoded by the mRNA translational "start" signal AUG which, in the particular case of E. coli expression exemplified, is not processed away by host systems. In other microbial systems, e.g., pseudomonas, methionine may be removed; it does not in any event appear required for activity. Where methionine is removed and depending upon the system employed, the GLN residue may cyclize to the pyroglutamate form, again without any believed impairment of activity.

In our hands, the CYS-TYR-CYS- containing recombinant gamma interferon earlier reported by Gray and co-workers benefited from formulation with human serum albumin in aid of stabilization. The presence of serum albumin in the final lyophilized product, however, requires that certain quality control steps be performed in advance of lyophilization rather than upon finished product. In the case of the novel recombinant gamma interferon of present invention, on the other hand, the material in lyophilized form has proven to be sufficiently stable without the inclusion of serum albumin. Where desired, however, the gamma interferons of the invention may be formulated with pharmaceutically acceptable levels of human serum albumin.

Beyond the foregoing, the CYS-TYR-CYS- lacking recombinant human gamma interferons of the invention appear in cytopathic effect inhibition testing to be markedly more active as antiviral agents than their CYS-TYR-CYS-containing analogs. The activity is conventionally assayed in microtiter plates by inhibition of the cytopathic effect (CPE) of encephalomyocarditis virus on human lung carcinoma cells A549. See (12).

The recombinant gamma interferons of the invention include all those comprising amino acids i to about 126 of the full sequence provided above. Gamma interferons variously truncated at the carboxy terminal end relative to the full sequence continue to exhibit the characteristic properties of human gamma interferon, albeit at diminished levels in some cases, so long as amino acids 1 to about 126 are present. Indeed, experiments with the CYS-TYR-CYS- containing analog reported at (7) showed that extraneous sequences could be substituted for the amino acid sequence following amino acid 132 (by the present numbering system) without loss of activity. See, e.g., (8). Preliminary evidence in our hands supports the hypothesis that while amino acids I to about 126 (THR) are relatively tightly bound in a three-dimensional configuration we associate with activity, remaining amino acids of the full sequence are by comparison less confined and relatively sensitive to proteolysis. Trypsin digestion under limiting conditions removes various portions of the sequence downstream from amino acid 126, but not upstream therefrom. Native gamma interferon moieties in our hands include molecules variously extending through amino acids 127, 128, 129, 130, 132 and 134. We have seen fully active recombinant gamma interferon whose amino acid sequence following methionine consisted variously of amino acids (beyond MET) 1 to about 139 and 1 to about 131, the latter obtained by limited digestion of recombinant gamma interferon with trypsin followed by sequence confirmation. Similar trypsin digested fragments variously ending at about amino acids (beyond MET) 128 and 129 retained activity, albeit substantially diminished. On the other hand, material having 125 amino acids (in addition to N-terminal methionine), the threonine at position 126 and following amino acids having been digested away, exhibited less than 1% the activity of undigested material in CPE inhibition assay.

Recombinant derived gamma interferon, in addition to its bearing an initial methionine when produced in hosts where the methionine is not intracellularly cleaved, appears to exhibit a major species having 139 amino acids (based on the numbering system FIG. 1 (FIG. 1A and FIG. 1B) and a minor species having 143 amino acids. The composition of the two species contains greater than about 95 percent, most preferably greater than about 97 percent of the species having 139 amino acids. Trypsin digestion under limiting conditions likewise removes various portions of the sequence downstream from about amino acid 126. Recombinant gamma interferon in our hands following such limiting trypsin digestion include species variously extending through amino acids 125, (126 with an initial methionine) 129, 131 and 134. These species have retained activity, albeit substantially diminished, in the zone extending from about amino acid 125 to about 129. Species having at least about 129 amino acids, and especially at least about 131 amino acids, i.e., species having from about 129 to 143 amino acids are essentially functionally fully active.

In view of the foregoing, it will be apparent that the invention comprises not only recombinant gamma interferons exhibiting the full sequence depicted above, but also those, and mixtures of various of those, in which amino acid 143 is absent or in which the amino acid sequence Z→ amino acid 143 is absent, Z being amino acid 127, 128, 129, 130, 131, 132, 133, 134, 135, 136, 137, 138, 139, 140, 141 or 142. It will likewise be apparent that double stranded DNA sequences encoding recombinant gamma interferons according to the invention comprise not only those encoding the full sequence depicted above, but also those encoding only the various carboxy terminal—truncated analogs just described, in the case of each different truncation the following codon(s) encoding translation stop signal(s).

By reference to "recombinant gamma interferon" herein we intend a polypeptide (whether or not glycosylated by the cell in which it is produced) expressed in a transformant cell from a replicable expression vehicle arising from recombinant DNA technology, the polypeptide exhibiting in greater or less degree the antiviral and antiproliferative activity in humans and pH 2 labile properties characteristic of native human gamma interferon.

The recombinant gamma interferons described herein are believed to form "dimers", defined for the purpose of this disclosure as a combination of two such polypeptides each having at least the 1 to about 126 amino acids (which polypeptides may have the same or a different number of amino acids). The nature of the chemical combining mechanism is not fully understood, but is believed to be other than covalent bonding. This combination into dimers appears to occur spontaneously and is believed to be inevitable in the systems described herein. Thus, when the recombinant gamma interferons of the present invention are administered, they will usually be in the dimerized form.

Furthermore, it is to be understood that here, similarly to the disclosures in the literature relating to differently characterized recombinant gamma interferons (8, 9), amino acid substitutions or additions, particularly single amino acid substitutions and addition or substitution of groups of amino acids upstream or downstream from about amino acid 126 or the C-terminus, in the recombinant gamma interferons disclosed herein are possible without destroying the interferon activity which they possess. It is believed that it will be obvious to those skilled in the art to make such substitutions or additions without departing from the scope of the present invention. Again, the recombinant gamma interferons of the present invention include species having modifications and allelic variations of the full sequence (see FIG. 1 (FIG. 1A and FIG. 1B)) which exhibit biological activity equivalent to or greater than that of the full sequence.

Characteristically, purified recombinant gamma interferons will be essentially free of other proteins of human origin, and are so to be distinguished from the native human gamma interferon compositions heretofore available.

The invention includes recombinant gamma interferon compositions which (prior to formulation) are greater than about 95 percent pure, preferably more than about 98 percent pure, which compositions are for that reason likewise distinct from native gamma interferons heretofore available.

Embodiments of the invention in which the N-terminal amino acid residue is methionyl are likewise distinct from gamma interferons produced within the human body, and appear also for that reason to be distinct, beyond their deletion of CYS-TYR-CYS-, from those whose sequence is reported by Gray et al. (6).

The replicable expression vehicles referred to herein are double- stranded DNA moieties, preferably plasmids, comprising an origin of replication, a promoter or promoter-operator, a sequence encoding a ribosome binding site, a codon for a translation start signal, and in proper reading phase therewith a gene encoding the recombinant gamma interferon of interest, followed by codon(s) for a translation stop. At the present stage the general techniques and lexicography of recombinant DNA technology are well understood to the art-skilled, who are referred in any event to (11) for background information pertinent to the practice of the present invention, mutatis mutandis, in all its embodiments and legally cognizable equivalents.

EXAMPLE

A. Cloning

Recombinant DNA clones containing gamma interferon cDNA sequences were prepared as described in (6) and in the aforementioned related application Ser. No. 06/312,489, now abandoned, with messenger RNA from induced human peripheral blood lymphocytes. The DNA sequence of clone p67 is shown in FIG. 1 (FIG. 1A and FIG. 1B). A 5' untranslated region is followed by 69 nucleotides encoding a precursor or signal peptide of 23 amino acids, 429 nucleotides coding for a mature interferon polypeptide of 143 amino acids, and 587 nucleotides of 3' untranslated sequence.

B. Expression

1. *E. Coli* Example

To express high levels of recombinant IFN-$_\gamma$ in *E. coli*, the initiation of protein synthesis must occur at an ATG codon immediately preceding the glutamine codon (amino acid one) of the mature polypeptide rather than at the ATG of the signal peptide (amino acid S1) (FIG. 1 (FIG. 1A and FIG. 1B)). The procedure followed to express the cDNA insert of p67 directly in *E. coli* is outlined in FIG. 2. The approach was similar to that used to express in *E. coli* the cDNA insert of Gray et al. (6).

An AvaII restriction site located at codon 2 of the presumed mature coding sequence was utilized to remove the signal peptide coding region. Two synthetic deoxyoligo-nucleotides were designed which restore the codons for amino acids 1 and 2, incorporate an ATG translational initiation codon, and create an XBaI cohesive terminus. These two oligomers were ligated to the remainder of the cDNA insert to construct a 1063 base-pair synthetic-natural hybrid gene coding for a polypeptide of 144 amino acids and bounded by XBaI and PstI sites. This gene was inserted into the plasmid pLeIF A25 (10) between the XBaI and PstI sites to give the expression plasmid p$_\gamma$-CYC5. *E. coli* strain W3110 (F-, λ-, protrophic) (ATCC No. 27325) was transformed with this plasmid to give the host-vector combination *E. coli* W#110/py-CYC5.

2. Cell Culture Example

Expression of a gene encoding both the signal peptide and gamma interferon, as indicated in FIG. 1 (FIG. 1A and FIG. 1B), was effected in COS-7 cells (16) in the presence of radioactively labeled cysteine and methionine, confirming the production from the gene of mature gamma interferon whose N-terminal amino acids are as indicated in FIG. 1 (unlike the case involving *E. coli* expression, the expression product of mammalian cell systems like that exemplified here lacks N-terminal methionine).

Confluent monolayers of COS-7 cells in 60 mm petri dishes were transfected in duplicate with DNA using the modified DEAE-dextran procedure. Three days after DNA addition, the media was removed. Each set of plates received 2 mls DMEM supplemented with either 100 μCi S$^{35}$-methionine or S$^{35}$-cysteine. After 16 hours incubation in the presence of the radiolabeled amino acid, the media was removed and 500 μl immunoprecipitated using an anti-gamma-interferon monoclonal antibody or an anti-HBsAg monoclonal antibody as the first antibody and a rabbit anti-mouse IgG antibody (Cappell Inc.) as the second antibody. Reaction with the antibody and the subsequent binding to Staphlycoccus A cells (Calbiochem) are as described by Berman, P. et al. (18). The samples were resuspended in SDS-mercaptoethanol and electrophoresed on 10Δ SDS-PAGE gels. The gel was fixed in 7Δ acetic acid in ethanol, soaked in Enhance (New England Nuclear) fluor solution, dried down, and exposed for two weeks using Kodak AR5 film and an intensifying screen (Dupont).

Plasmids used in this study were pSVgamma69 (11); pDL RI (19), a hepatitis B virus surface antigen expression vector upon which pSVgamma69 was based; and pDL Rlgamma Sau, a polycistronic plasmid containing the 830 bp SAU3a fragment of pSVgamma69 (11) spanning the entire gamma-interferon encoding sequences inserted into the EcoRI site of pDL RI. The latter plasmid produces a transcript containing both the gamma-interferon and the HBsAg coding regions.

Comparison of S$^{35}$-Cysteine and S$^{35}$-Methionine labeled proteins which react with either anti-gamma-interferon (A) or anti-HBsAg (B) antibodies showed that no material migrating at either the glycosylated (29,000 MW) or monoglycosylated position (18,000 MW) was specifically immunoprecipitated from S$^{35}$-Cys labeled pDL RI-gamma Sau transfected cells using anti-gamma-interferon antibody, in contrast to the S$^{35}$-met labeled cells which showed the immunoprecipitation of interferon-gamma.

C. Fermentation Production

The production of recombinant Human Interferon—Gamma (rIFN-$_\gamma$) using *E. coli* W3110/p$_\gamma$- CYC5 is carried out in batches ranging in volume from 10 to 1000 liters. After fermentation, the interferon containg *E. coli* cells are recovered from the broth for isolation and purification of rIFN-$_\gamma$. The following is a description of the fermentation and cell recovery processes.

1. Preparation and Maintenance of Stock Cultures

A stock culture is prepared in sterile baffled culture flasks containing 150 to 500 mL of a sterile medium having the following composition.

Bactotryptone 10 g/L
Yeast Extract 5 g/L
Sodium Chloride 5–10 mg/L

The medium is then inoculated with a primary culture of *E. coli* W3110/p$_\gamma$-CYC5.

The inoculated flask is then incubated on a shaker at 25°–37° C. until the absorbance at 550 nm reaches approximately 1.0. Approximately 50 percent v/v of 30 percent v/v dimethyl sulfoxide is added to the broth. One (1) mL aliquots are immediately dispensed into sterile vials and capped. The vials are stored at −60° C. or below. Each fermentation is started using a replicate stock culture for inoculum.

2. Inoculum Preparation

The inoculum is prepared in the medium previously described (L. B. Broth) in either shaker flasks or small fermenters. After incubation at about 37° C. for approximately 8 hours, the inoculum is transferred to a fermenter. The volume of the inoculum is between 2 to 10 percent of the volume of the fermentation.

3. Fermentation

Recombinant Interferon—Gamma production is carried out in fermenters with working volume of about 10 to 1000 liters. The fermentation medium is composed of:

|  | Per liter |
| --- | --- |
| *Glucose | 50–100 g |
| Ammonium Sulfate | 4.0–8.0 g |
| Potassium Phosphate, Monobasic | 3.0–5.0 g |
| Potassium Phosphate, Dibasic | 5.0–8.0 g |
| Magnesium Sulfate, Heptahydrate | 0.5–5.1 g |
| Sodium Citrate, Dihydrate | 0.5–2.0 g |
| UCON LB-625 | 0.5–2.0 mL |
| Ferric Chloride, Hexahydrate | 0.005–0.15 g |
| Zinc Sulfate, Heptahydrate | 0.001–0.15 g |

| | Per liter |
|---|---|
| Cobalt Chloride, Hexahydrate | 0.001–0.005 g |
| Sodium Molybdate, Dihydrate | 0.001–0.005 g |
| Cupric Sulfate, Pentahydrate | 0.001–0.005 g |
| Boric Acid | 0.001–0.005 g |
| Manganese Sulfate, Monohydrate | 0.001–0.005 g |
| Hydrochloric Acid | 0.0–1.0 mL |
| Thiamine-HCl | 0.0–0.1 g |
| Tetracycline HCl | 0.001–0.01 g |
| *L-Tryptophan | 0.1–0.5 g |
| Yeast Extract | 2.0–8.0 g |
| 3-β-Indoleacrylic acid | 0.02–0.10 g |

*A portion of the glucose and tryptophan is added to the fermenter initially and the remainder is fed throughout the fermentation process.

Ingredients in the medium are sterilized by heat treatment or filtration prior to use in fermentation.

The fermentation is carried out at 25°–40° C. Other operating conditions are as follows:

| Agitation (rpm) | 100–1000 | |
|---|---|---|
| Aeration (vvm) | 0.5–1.5 | (Supplemented with oxygen when necessary) |
| pH | 6.5–7.5 | (Controlled by the addition of ammonium hydroxide) |

4. Purification a. Extraction of Recombinant Gamma Interferon.

E. coli cells are suspended in a medium which contains salts and an appropriate buffer in the pH range of 6 to 9, preferably about 9. Recombinant gamma interferon is extracted by homogenization of the cell suspension in a high pressure colloid mill such as a Gaulin mill. Sufficient polyethyleneimine is added to the solution to produce a 0.1 to 1% W/V solution. The supernatant contains gamma interferon.

b. Partial Purification of Recombinant Gamma Interferon on a Silica-based Adsorbant.

The supernatant from part (a) is adsorbed to a silica based adsorbant which is washed to remove impurities with appropriate salt solutions in the pH range of 6 to 9. Recombinant gamma interferon is eluted using a solution containing 0.5–1.0M tetramethyl ammonium chloride. All operations in this step are performed in the pH range of 7 to 9.

c. Partial Purification of Recombinant Gamma Interferon by Anion Exchange Chromatography The eluate from part (b) is dialysed and adsorbed to an anion exchange chromatography medium which is then washed to remove impurities. Recombinant gamma interferon is eluted with a gradient of increasing salt. Typical anion exchange resins applicable for this step include carboxymethyl cellulose and sulphoethyl cellulose. All operations are performed in the pH range of between 7 and 9.

d. Partial Purification of Recombinant Gamma Interferon by Chromatography on Calcium Phosphate Gel The eluate from part (c) is adsorbed to a medium of calcium phosphate which is then washed to remove impurities. The recombinant gamma interferon is eluted by increasing the salt concentration in a gradient of increasing phosphate concentration. All operations in this step are performed in the pH range of between 7 and 9.

e. Partial Purification of Recombinant Gamma Interferon by Anion Exchange Chromatography The eluate from part (d) is dialysed and adsorbed to an anion exchange chromatography medium which is then washed to remove impurities. The recombinant gamma interferon is eluted from the anion exchange medium with a gradient of increasing salt concentration. Typical anion exchange chromatography media are carboxymethyl cellulose and sulphoethyl cellulose. All operations in this step are performed in the pH range of between 7 and 9.

f. Partial Purification of Recombinant Gamma Interferon by Gel Permeation Chromatography.

The eluate from part (e) is applied to a gel permeation medium and the column is developed with a salt containing medium. The appropriate recombinant gamma interferon containing fractions are pooled to produce the bulk drug substance. All operations in this step are performed in the pH range of between 7 and 9.

g. C-Terminal Amino Acid Sequence

To determine the c-terminal sequence samples were dialyzed into 70 percent formic acid, cleaved with cyanogen bromide and the resulting peptides separated on an Altex Ultrasphere C8 reverse phase HPLC column. Peaks were collected and analyzed by amino acid and sequence analysis. One C-terminal peptide was found: -leu-phe-arg-gly-arg (residues 135–139, FIG. 1 (FIG. 1A and FIG. 1B)). In some cases another additional peptide was detected: -leu-phe-arg-gly-arg-arg-ala-ser-gln (residues 135–143, FIG. 1). To determine the ratio of these two peptides, known amounts (by amino acid analysis) were loaded onto the reverse phase HPLC column and the respective peak heights determined. Each of three production lots contained less than about two percent of the long peptide (135–143, FIG. 1 (FIG. 1A and FIG. 1B)), the balance being the 5-mer. These data are consistent with E. coli production of a mixture of 139 amino acid-containing and 143 amino acid-containing gamma interferons (excluding the N-terminal methionine, which is also present in each case) in the relative proportions, respectively, of about 98.2 percent.

5. Formulation

Recombinant gamma interferon made in accordance with the foregoing is preferably formulated for parenteral administration according to the following Table.

| | QUANTITY PER VIAL | |
|---|---|---|
| Ingredient | 0.5 mg vial (1) | 2.0 mg vial (2) |
| Recombinant Human Interferon - Gamma | 0.5 | 2.0 |
| Mannitol | 100 | 80 |
| Succinic Acid Disodium Hexahydrate | 12.4 | 9.9 |
| Glycine | 5.6 | 4.5 |
| Sodium Chloride | 4.4 | 3.5 |
| Polysorbate 20 | 0.8 | 0.6 |
| Succinic Acid | 0.5 | 0.4 |

(1)Vials are reconstituted with 2.5 ml sterile Water for Injection.
(2)Vials are reconstituted with 2.0 ml sterile Water for Injection.

The interferons of the invention may be employed in medically appropriate dosage ranges, e.g., 1.0 mg/$M^2$ of body surface area.

D. Determination of the Activity of Various Gamma Interferons Following Trypsin Digestion To establish the activity of various gamma interferons differing in their carboxy-termini gamma interferon prepared as describd in the E. coli example, supra, was digested with trypsin to various degrees and tested by CPE assay with A549 cells as described within.

A sample of recombinant gamma interferon (r-HuIFN-gamma) (6.5 mg), prepared as described herein, was desalted over a small Sephadex G-25 molecular sieving column (PD-10, Pharmacia) into 0.10 M Ammonium Bicarbonate buffer, pH 8.5 to a final protein concentration of 2.1 mg/ml. A dilute trypsin solution (Worthington TPCK trypsin, 10 µg/ml in 0.001M HCl, 16 µl) was added to 1.9 ml (4.0 mg) of the r-HuIFN-gamma solution, mixed and incubated at room temperature (trypsin:protein:1:25,000). Samples were removed from the incubation mixture at 1 hr., 3.5 hrs., 5.75 hrs., 8 hrs. and 10.25 hrs. At 8 hrs., an additional 15 µl (150 ng) of dilute trypsin solution was added in order to accelerate the reaction for the last time point sample at 10.25 hrs.

Fractionation of each time point sample into its respective components was performed on a Waters HPLC system using a BioRad Biogel HPHT Column. The time point aliquot in bicarbonate buffer was loaded directly (by manual injection) to the column at the time of sampling. The column was equilibrated in 0.01M sodium phospate pH 8.0, 30 µM calcium chloride and protein was eluted from the column utilizing a linear gradient of the equilibration buffer and 0.5M sodium phosphate buffer pH 8.0, 0.6 µM calcium chloride.

Protein peaks as determined by absorbance at 214 nm and 280 nm were preparatively collected and stored covered at 4° C. until analyzed. Typical analyses for selected peaks included:

1. Antiviral activity in the human lung carcinona A549/EMC virus assay system (13).
2. SDS/PAGE fractionation by standard techniques employing the Laemmli gel system (14).
3. Protein concentration determination by the commercial (Pierce Chemical Co., Rockford, Ill.) dye binding procedure.
4. Cyanogen bromide protein cleavage and subsequent HPLC analysis for peptide identification (15).

Samples of protein are dialyzed (12,000–14,000 mw cut off) overnight against 70% formic acid, taken to dryness by rotary evaporation and resuspended in 500 µl of 70% formic acid. Solid cyanogen bromide is added to each sample in a 12×75 mm glass tube, sealed, mixed until dissolved, covered with aluminum foil and incubated overnight at room temperature in a well ventilated area.

After cleavage, samples are taken to dryness by rotary evaporation, resuspended in 0.5 ml of water and redried. Prior to fractionation by HPLC, samples were redissolved in 50% formic acid to a protein concentration of approximately 1 mg/ml.

Peptides were fractionated using a Waters HPLC system employing an Altex Ultrasphere Octyl column and a trifluoroacetic acid/water—trifluoroacetic acid/acetonitrile linear elution gradient. Wherever possible, peptides were identified by amino acid analysis. Table I lists comparative data for shortened forms of r-HuIFN-γ:

TABLE 1

| r-HuIFN-γ Form* | C-Terminus** | Specific Activity (%) |
|---|---|---|
| 139aa:143aa::98:2 (for comparison) | LFRGR | 100 |
| 131aa | AAKTGKRKR | 40–50 |
| 129aa | AAKTGKR | 6–9 |
| 125aa | AAK | ca. 1 |

*Based on numbering system of FIG. 1 (FIG. 1A and FIG. 1B), but excluding the N-terminal methionine also present in each case.
**Conventional single letter abbreviations for amino acid residues:
A = alanine
F = phenylalanine
G = glycine
K = lysine
L = leucine
R = arginine
T = threonine It will be appreciated that gamma interferons of any length within the range 126aa–143aa (excluding N-terminal methionine) will be expressed from appropriately tailored genes. Thus, for example, the gene depicted in FIG. 1 (FIG. 1A and FIG. 1B) contains a Fnu4H restriction site at

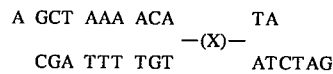

Following restriction with Fnu4H, synthetic oligonucleotides encoding any desired sequence followed by a "stop" codon and a linker compatible with an available restiction site in the expression plasmid may be ligated to the fore part of the gamma interferon gene. For example, the sequence

A GCT AAA ACA          TA
          —(X)—
  CGA TTT TGT       ATCTAG wherein X encodes one or more amino acids may be ligated into the E. coli expression vehicle exemplified above following digestion of the plasmid with Fnu4H and BglII, a stop codon resulting from ligation thusly

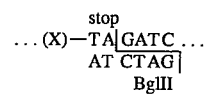

E. Assay: Inhibition of Cytopathic Effect (CPE)

1. Test Procedure

To each well add 100 microliters of a suspension of human lung carcinoma (A549) cells (ATCC No. CCL 185) which have been adjusted to contain $4 \times 10^5$ cells/ml in Eagles MEM.

Incubate plates at 37° C. for approximately 18 hours.

After 18 to 24 hours incubation, add to each well in the first column, 80 microliters additional medium.

Add to a well in the first column 20 microliters of a sample to be assayed for interferon activity.

Transfer 100 microliters of the contents of each well in the first column horizontally to each well in second column.

Continue to transfer 100 microliters of the contents of a well from column to subsequent column until a total of 10 transfers are performed ending in column 11.

After 24 hours of incubation, challenge all wells, except cell controls, with 50 microliters of encephalomyocarditis virus at a multiplicity of infection which results in 100% cytopathic effect in 24 hours after infection.

Cover trays with lids and incubate at 37° C. for 24 hours.

Pour off fluid from all wells and stain 5–15 minutes with 0.5% crystal violet.

Viability of cells is determined by observation of stained cells.

Titer of a sample is the reciprocal of the dilution where 50% viable cells remain.

2. Calculation

The activity of all samples is normalized by the Reference Units Conversion Factor which is calculated from:

$$\frac{\text{Actual Titer of Standard Interferon}}{\text{Observed Titer}} = \text{Reference Units Conversion Factor} = RUCF$$

3. Specific Activity

Using the A549/EMCV bioassay systems standardized with IFN-gamma reference material provided by the NIH, the specific antiviral activity of recombinant human IFN-gamma is approximately three times higher than the activity of the modified rIFN-gamma molecule with three additional amino acids (cys-tyr-cys) at the N-terminus.

4. Stability

Based again on the above mentioned measure of bioactivity (A549/EMCV), formulated and vialed rIFN-gamma continues to be stable (no loss of biological activity) three months after production (stored at 4° C).

F. Antiproliferative activity of rIFN-gamma compared to the other types of human interferon 1. Materials and Methods rIFN-gamma: Des Cys-Tyr-Cys recombinant interferon gamma in the form of a solution (20 mM sodium succinate, 0.15M NaCl, pH 6). The material was prepared in accordance with the *E. coli* Example above. The specific activity was $2.7 \times 10^7$ IU/mg protein.

CTC-rIFN-gamma: Recombinant interferon gamma having "Cys-Tyr-Cys" structure at the N-terminus of the molecule in the form of a solution (20 mM sodium succinate, 0.15M NaCl, pH 6). The specific activity was $1.3 \times 10^7$ IU/mg protein.

HuIFN-beta: Lyophilized human fibroblast interferon produced in human diploid foreskin fibroblast with a specific activity of more than $1 \times 10^7$ IU/mg protein prepared by Toray Ind., Inc. A vial contains $3 \times 10^6$ IU HuIFN-beta and 3 mg human serum albumin.

HuIFN-alpha: Human natural leukocyte interferon with a specific activity of $4 \times 10^6$ IU/mg protein supplied in the form of solution by Dr. K. Cantell, Central Public Health Laboratory, Helsinki, Finland.

Control: Placebo containing 3 mg human serum albumin.

Culture Medium: Eagle's minimum essential medium supplemented with 10 percent heat-inactivated precolostrum newborn calf serum ("PNCS") and 2 mM L-glutamine was used with Hela, KB, HMV-1, FL, and J-111 cells. Dulbecco's minimum essential medium containing 10 percent heat-inactivated PNCS, 100 µg/ml kanamycin, and 2 mM L-glutamine was used with A549 cells. RPMI 1640 medium supplemented with heat-inactivated PNCS and 100 µg/ml kanamycin was used with the remaining human cells listed in Table 2.

2. Evaluation of antiproliferative activity

The test cells suspended in the culture medium were seeded into plastic tissue culture plates at a concentration of $5 \times 10^3$ cells/0.5 ml/well. Various amounts of interferon dissolved in the corresponding culture medium (0.5 ml) were added subsequently (day 0). Cultivation was carried out at 37° C. in a humidified atmosphere of 5 percent $CO_2$ and 95 percent air. On day 6 the culture media were removed and the cells in suspension culture were directly suspended in Isoton II (Coulter Electronics Inc.) for cell counting in a Coulter counter. The cells forming a sheet in plastic vessels were pre-treated with 0.05 percent trypsin-0.02 percent EDTA to prepared single cell suspension in Isoton II (Coulter Electronics Inc.). Antiproliferative activity of interferon was expressed as the antiviral units required to produce 50 percent reduction of cell number ($IC_{50}$, IU/ml) compared to the control culture (without interferon).

As shown in the table, the antiproliferation activity of rIFN-gamma varied markedly depending on the human cell species. In this case KATO-III, siglet-ring cell carcinoma of the stomach, was highly sensitive, the cell line showing the $IC_{50}$ of 1.2 IU/ml, while Daudi cells, Burkitt's lymphoma, which were highly sensitive to type II interferon (HuIFN-alpha, HuIFN-beta), were insensitive to type II interferon including rIFN-gamma. Lung adenocarcinoma (PC-8, PC-12) was insensitive to all interferon species tested. The anticellular spectrum between rIFN-gamma and CTC-rIFN-gamma was almost the same and it was generally apparent that the antiproliferative efficacy of rIFN-gamma was superior to that of CTC-rIFN-gamma. In the case of comparison between four interferons, the highest efficacy was obtained from rIFN-gamma except for Daudi cells.

G. Comparison of stability between rIFN-gamma and CTC-rIFN-gamma in various fluids in vitro $1 \times 10^6$ IU/vial of lyophilized rIFN-gamma prepared in accordance with the *E. coli* Example above and $1 \times 10^6$ IU/vial of lyophilized rIFN-gamma having a "Cys-Tyr-Cys" structure at the

TABLE 2

ANTIPROLIFERATIVE ACTIVITY OF rIFN-γ COMPARED TO OTHER INTERFERON SPECIES

| | | $IC_{50}$ (IU/ml) | | | |
|---|---|---|---|---|---|
| Cell | Histological Type or Origin of Test Cells | rIFN-γ | CTC-rIFN-γ | HuIFN-β | HuIFN-α |
| KATO-III | Siglet-ring cell carcinoma of stomach | 1.2 | 1.3 | — | — |
| MKN-1 | Adenosquemous carcinoma of stomach | 37 | 330 | — | — |
| MKN-28 | Well differentiated adenocarcinoma of stomach | >$10^3$ | >$10^3$ | — | — |

TABLE 2-continued

ANTIPROLIFERATIVE ACTIVITY OF rIFN-γ COMPARED TO OTHER INTERFERON SPECIES

| Cell | Histological Type or Origin of Test Cells | $IC_{50}$ (IU/ml) | | | |
|---|---|---|---|---|---|
| | | rIFN-γ | CTC-rIFN-γ | HuIFN-β | HuIFN-α |
| MKN-45 | Poorly differentiated adenocarcinoma of stomach | $>10^3$ | $>10^3$ | — | — |
| MKN-74 | Well differentiated adenocarcinoma of stomach | $>10^3$ | $>10^3$ | — | — |
| Hela | Uterine cervix carcinoma | 22 | 132 | 446 | $>10^3$ |
| KB | Nasopharyngeal carcinoma | 54 | 330 | $>10^4$ | $>10^4$ |
| HMV-1 | Amelanotic melanoma | 38 | 45 | 130 | 820 |
| SEKI-F | Melanoma | 135 | $>10^3$ | 137 | 663 |
| FL | Amnion (non-malignant origin) | 38 | 45 | $>10^3$ | $>10^4$ |
| PC-8 | Lung poorly differentiated adenocarcinoma | $>10^3$ | $>10^3$ | $>10^4$ | $>10^3$ |
| PC-12 | Lung adenocarcinoma | $>10^3$ | $>10^3$ | $>10^4$ | $>10^3$ |
| A549 | Lung alveolar carcinoma | 55 | — | — | — |
| QG56 | Lung squamous cell carcinoma | 5 | — | — | — |
| QG90 | Lung anaplastic small cell carcinoma | 5.5 | — | — | — |
| Daudi | Burkitt's lymphoma | $>10^3$ | $>10^3$ | 47 | 7 |
| Namaiwa | Burkitt's lymphoma | $>10^3$ | $>10^3$ | — | — |
| J-111 | Monocytic leukemia | 25 | 84 | 204 | $>10^3$ |

N-terminus, with 10 mg human serum albumin, phosphate buffer and an isotonic amount of NaCl for each interferon were reconstituted with distilled water and the concentration was adjusted to $4\times10^4$ IU/ml.

In vitro stability of interferons was evaluated by the determination of the residual anti-viral activity in various fluids. Incubations were initiated by addition of the above interferon solutions into nine volumes of rabbit serum, human serum or Eagle's MEM which were pre-incubated 10 min. in a water bath incubator at 37° C. or 4° C. At 0, 0.25, 0.5, 1, 4, 8, 24, 72 and 144 hr., an aliquot was harvested and mixed with the nine volumes of Eagle's MEM. The samples were kept frozen at −80° C. in a deep freezer until the assay of interferon titer. Interferon titer was assayed by the CPE50 reduction method using human amniotic cells (FL cell) challenged with Sindbis virus. The results are indicated in FIG. 3 (FIG. 3A, FIG. 3B, FIG. 3C, FIG. 3D, FIG. 3E, FIG. 3F) as percentages of residual titer against the additional titer.

While the invention has been exemplified by reference to the preferred embodiments in which expression is effected in E. coli and in COS-7 cells, it will be apparent that the recombinant gamma interferons of the invention may be produced in other systems as well such as other bacterial strains, yeast and tissue culture systems, as to which see related application Ser. No. 06/312,489, now abandoned, and (6). Thus, the invention is not confined to the most preferred embodiments, but instead extends to all legally cognizable equivalents of the claims which follow.

Bibliography

1. Goeddel, D. et al., Nature 287, 411 (1980)
2. Goeddel, D. et al., Nature 290, 20 (1981)
3. Yelverton, E. et al., Nucleic Acids Research 93, 731 (1981)
4. Gutterman et al., Annals of Int. Med. 93, 399 (1980)
5. Goeddel, D. et al., Nucleic Acids Research 8, 4057 (1980)
6. Gray, P. et al., Nature 295, 503–508 (1982)
7. Derynck, R. et al., Nucleic Acids Research 10, 3605 (1982)
8. Derynck, R. et al., Interferon Scientific Memoranda, August 1982, Memo-I-A1193/2.
9. Derynck, R. et al., "Expression of Human Interferon Gamma in Heterologous Systems" in Experimental Manipulation of Gene Expression, Academic Press, Inc. (1983) at 247
10. Goeddel, D. et al., Nature 287, 411–416 (1980)
11. European Patent Application of Goeddel, D. et al., EPO publication No. 0 077 670.
12. W. E. Stewart II in "The Interferon System" Springer Verlag (New York) pp. 13–26 (1979).
13. Stewart, "Interferon Systems" 'Ed.: Stewart, p 13 Springer-Derlag, New York (1979)
14. Laemmli, Nature 227, 680 (1970)
15. Gross, et al., Methods in Enzymology, XI, 238
16. Gluzman, Cell 23, 175 (1981)
17. Alton et al., "Production, Characterization and Biological Effects of Recombinant DNA Derived Human IFN-alpha and IFN-gamma Analogs," The Biology of the Interferon System, DeMaeyer and Schellekens, Eds., Elsevier Science Publ. (1983).
18. Berman et al., Science 222, 524 (1983)
19. Simonsen et al., Mol. Cell. Biol. 3, 2250 (1983)

We claim:

1. A process of preparing a composition of matter comprising interferon polypeptides, wherein said interferon polypeptides consist essentially of:

a first polypeptide having an amino acid sequence consisting of an N-terminal group X-Y- joined to residues $Asp^2$ through $Arg^{139}$ of the interferon-γ amino acid sequence shown in FIGS. 1A–1B, and a second interferon polypeptide having an amino acid sequence consisting of an N-terminal group X-Y- joined to residues $Asp^2$ through $Ser^{142}$ or $Gln^{143}$ of the interferon-γ amino acid sequence shown in FIGS. 1A–1B, wherein the N-terminal group X-Y is selected from the group consisting of Met-Gln, H-Gln, and H-pyroglutamate; said method consisting essentially of:

providing transformed host cells comprising a single species of heterologous interferon DNA, wherein said DNA is present in an operative expression vector and comprises codons for Met-Gln joined to codons for residues $Asp^2$ through $Gln^{143}$ of the interferon-γ amino acid sequence shown in FIGS. 1A–1B, culturing said host cells under conditions suitable for the expression of said DNA and the production of said interferon polypeptides, and recovering said interferon polypeptides.

2. A process according to claim 1, wherein the N-terminal group X-Y is Met-Gln.

3. A process according to claim 1 or 2, wherein said first polypeptide constitutes at least about 95% of said interferon polypeptides.

4. A process according to claim 1 or 2, wherein said first polypeptide constitutes at least about 97% of said interferon polypeptides.

5. A process according to claim 1, wherein said step of recovering the interferon polypeptides comprises purifying said polypeptides.

* * * * *